United States Patent [19]

Jordan et al.

[11] Patent Number: 5,076,953

[45] Date of Patent: * Dec. 31, 1991

[54] SKIN CLEANSING SYNBARS WITH LOW MOISTURE AND/OR SELECTED POLYMERIC SKIN MILDNESS AIDS

[75] Inventors: Neil W. Jordan; William M. Winkler; Martha O. Visscher, all of Cincinnati; Sharon A. Seaman, Milford; Harold O. McGuffey, Cincinnati, all of Ohio

[73] Assignee: The Procter & Gamble Company, Cincinnati, Ohio

[*] Notice: The portion of the term of this patent subsequent to Jun. 16, 2004 has been disclaimed.

[21] Appl. No.: 305,244

[22] Filed: Feb. 1, 1989

Related U.S. Application Data

[63] Continuation-in-part of Ser. No. 97,997, Sep. 17, 1987, abandoned, and a continuation-in-part of Ser. No. 97,999, Sep. 17, 1987, abandoned, and a continuation-in-part of Ser. No. 62,258, Jun. 15, 1987, Pat. No. 4,812,253, which is a continuation of Ser. No. 733,670, May 13, 1985, Pat. No. 4,673,525.

[51] Int. Cl.$^5$ .......................... C11D 9/60; C11D 9/02
[52] U.S. Cl. .................... 252/108; 252/132; 252/117; 252/121; 252/122; 252/174.17; 252/DIG. 2; 252/DIG. 5; 252/DIG. 7
[58] Field of Search ........... 252/108, 122, 132, 174.17, 252/117, DIG. 2, DIG. 5, DIG. 7, DIG. 16

[56] References Cited

U.S. PATENT DOCUMENTS

| | | | |
|---|---|---|---|
| 2,894,912 | 7/1959 | Geitz | 252/121 |
| 2,979,465 | 4/1961 | Parran et al. | 252/546 |
| 2,988,511 | 6/1961 | Mills et al. | 252/121 |
| 3,043,778 | 7/1962 | Kelly | 252/121 |
| 3,598,746 | 8/1971 | Kaniecki et al. | 252/118 |
| 3,703,481 | 11/1972 | Barker et al. | 252/90 |
| 3,761,418 | 9/1973 | Parran | 252/106 |
| 4,012,341 | 3/1977 | Orshitzer et al. | 252/121 |
| 4,180,470 | 12/1979 | Tokosh | 252/121 |
| 4,234,464 | 11/1980 | Morshauser | 252/544 |
| 4,292,212 | 9/1981 | Melby | 252/547 |
| 4,338,211 | 7/1982 | Stiros | 252/541 |
| 4,477,375 | 10/1984 | Grollier | 252/542 |
| 4,491,539 | 1/1985 | Hoskins et al. | 252/541 |
| 4,540,507 | 9/1985 | Grollier | 252/174.23 |
| 4,574,053 | 3/1986 | Kinsman et al. | 252/134 |
| 4,673,525 | 6/1987 | Small et al. | 252/132 |
| 4,678,606 | 7/1987 | Akhter et al. | 252/542 |
| 4,812,253 | 3/1989 | Small et al. | 252/132 |
| 4,820,447 | 4/1989 | Medcalf | 252/117 |

FOREIGN PATENT DOCUMENTS

1065460 4/1967 United Kingdom ......... 252/DIG. 5

*Primary Examiner*—Paul Lieberman
*Assistant Examiner*—John F. McNally
*Attorney, Agent, or Firm*—Leonard Williamson; Robert B. Aylor; Richard C. Witte

[57] ABSTRACT

Disclosed is a mild skin cleansing bar composition comprising: mild synthetic surfactants, moisturizers, polymeric skin feel and mildness aids, selected levels of soap, and low moisture content to provide improved in use properties with regard to bar firmness and reduced messiness. Also disclosed is an ultra mild skin cleansing bar composition comprising: a mixture of selected polymeric skin feel and mildness aids and selected levels of soap. An ultra mild skin cleansing bar is provided which is clinically milder on the skin than water and has improved rinsing, firmness and reduced messiness.

27 Claims, No Drawings

SKIN CLEANSING SYNBARS WITH LOW MOISTURE AND/OR SELECTED POLYMERIC SKIN MILDNESS AIDS

CROSS-REFERENCE TO RELATED APPLICATIONS

This is a continuation-in-part of copending U.S. Ser. Nos. 097,997 and 097,999, both filed Sept. 17, 1987; as well as co-pending U.S. Ser. No. 062,258, filed June 15, 1987, now U.S. Pat. No. 4,812,253, small et al., issued Mar. 14, 1989, which, in turn, is a continuation of U.S. Ser. No. 733,670, filed May 13, 1985, now U.S. Pat. No. 4,673,525, issued June 16, 1987.

TECHNICAL FIELD

This invention relates to mild skin cleansing toilet bar compositions.

BACKGROUND OF THE INVENTION

This invention relates to mild skin cleansing toilet bars. More particularly, this invention relates to skin cleansing toilet bars comprising synthetic surfactants, moisturizers, polymeric skin feel and mildness aids and some soap.

The cleansing of skin with surface-active cleansing preparations has become a focus of great interest. Many people wash and scrub their skin with various surface-active preparations several times a day. Ideal skin cleansers should cleanse the skin gently, causing little or no irritation, without defatting and overdrying the skin or leaving it taut after frequent routine use. Most lathering soaps, liquids and bars included, fail in this respect.

Synthetic detergent bars, frequently referred to as "syndet bars," are well known and are becoming increasingly popular. However, widespread replacement of soap bars by syndet bars has not so far been possible for a variety of reasons, primarily the poor physical characteristics of syndet bars as compared to soap bars, e.g., smear or bar messiness and lather quality.

Certain synthetic surfactants are particularly mild. However, a major drawback of most mild synthetic surfactant systems when formulated for skin cleansing is poor lather performance, when compared to the highest bar soap standards (bars which are rich in coconut soap and superfatted). On the other side, the use of known high sudsing anionic surfactants with lather boosters can yield acceptable lather volume. Unfortunately, however, the highest sudsing anionic surfactants are, in fact, poor in clinical skin mildness. Surfactants that are among the mildest, such as alkyl (sodium lauryl) glyceryl ether sulfonate, (AGS), are marginal in lather. It will be appreciated that these two factors make the surfactant selection, the lather and the skin feel benefit formulation process, a delicate balancing act.

Similarly, optimization of bar firmness also requires a delicate balancing act with respect to maintaining acceptable lather and mildness, although as a single variable, bar firmness is accomplished through a fairly straightforward process with adjustments to levels of fillers, binders, etc., such as free fatty acids.

It is known that moisturizers provide skin conditioning benefits. For example, it is known that glycerin and/or free fatty acids are added to bars or liquid cleansing products for skin benefits.

Likewise, polymeric skin feel aids are known to those knowledgeable in the art for providing unique tactile characteristics to both the lather and the skin during rinsing.

For background, examples of liquid cleansing compositions are disclosed in the following references. U.S. Pat. No. 4,338,211, Stiros, issued July 6, 1982, discloses liquid skin cleanser with 2.3% to 3% AGS, the polymer JR-400 and small amounts of free fatty acid plus a fatty acid alkylolamide as lather boosting agents. Compositions containing the surfactants AGS and sarcosinate are not disclosed. Also, U.S. Pat. No. 4,491,539, James J. Hoskins and Adriaan Kessler, issued Jan. 1, 1985, discloses liquid cleansing products comprising about 5% to 30% of surfactant, about 0.1% to about 1.0% of guar material, about 0.15% to about 1.0% of nonionic carboxyvinyl polymer, and water. Exemplary compositions containing mild surfactants in general and, specifically, the surfactants AGS and sarcosinate are not disclosed. Another background reference is British Pat. No. 2,103,236A, Colgate, Feb. 16, 1984, which discloses a liquid detergent containing guar gum, a ternary surfactant mixture including betaine. AGS is not used.

U.S. Pat. No. 2,894,912, Geitz, issued July 14, 1959, for "Isethionate Detergent Bar," discloses a detergent bar consisting essentially of from 30-70% of water-soluble alkali metal detergent salts of esters of isethionic acid with mixed aliphatic fatty acids having from 6 to 18 carbon atoms and an iodine value of less than 20, of which mixed acids at least 75% have from 12 to 18 carbon atoms and up to 25% have from 6 to 10 carbon atoms, from 2-10% of at least one water-soluble suds-boosting detergent salt selected from the group consisting of alkali metal and organic amine higher aliphatic fatty alcohol sulfates, alkyl aryl sulfonates, and higher aliphatic fatty acid taurides, from about 1% to about 9% water, from about 2.5% to about 25% of water-soluble higher fatty acid soap, and from 10-40% of at least one higher fatty acid having from about 12 to about 25 carbon atoms as a binder and plasticizer, said bar having a pH within the range from 6 to 8, measured as a 10% aqueous solution of the bar composition at 35° C. This patent does not teach the use of polymeric skin feel aids nor the use of other mild synthetics.

U.S. Pat. No. 4,234,464, Morshauser, issued Nov. 18, 1980, for "Detergent Bar Composition and Binder Therefor," discloses a detergent bar in Example 6 which comprises: 45% sodium cocoyl isethionate, 5% alkyl amide, 37.5% stearic acid, 5.0% hydrogenated tallow glycerides, and 1% Polymer JR. Morshauser teaches that his detergent bars can contain up to 5% soap "without substantial detriment." This patent also teaches the use of up to 1.5% cationic polymer.

U.S. Pat. No. 4,012,341, Orshitzer et al., issued Mar. 15, 1977, for a "Unique All Synthetic Detergent Shampoo Bar," discloses a bar comprising a mixture of anionic and nonionic detergents. Examples 2 and 4 use 1% JR-400 in bars primarily based on sodium lauryl sulfate, which is an unacceptable surfactant for the present invention.

U.S. Pat. No. 3,761,418, Parran, Jr., issued Sept. 25, 1973, for "Detergent Compositions Containing Particle Deposition Enhancing Agents," discloses detergent compositions including a bar which contains 1% JR-400. However, the main surfactant is alkyl sulfate, which is unacceptable for the mild skin cleanser of the present invention.

Thus, in view of the above, it will be appreciated that rather stringent requirements for skin cleansers limit the choice of surface-active agents and final formulations represent some degree of compromise. Mildness is often obtained at the expense of effective cleansing and lathering. Conversely, mildness may be sacrificed for either preferred lathering characteristics, bar firmness, product stability, or all of these. Bars with only one polymer are disclosed in commonly assigned U.S. Pat. No. 4,673,525; Small/Garrison/Winkler/Seaman/Papa, issued June 15, 1987, incorporated herein by reference, but do not recognize the benefit disclosed herein.

OBJECTS OF THE INVENTION

This invention represents a skin cleansing toilet bar which provides improved skin feel and rinsing, ultra skin mildness, excellent lather, and bar firmness. Therefore, the object of this invention is the development of skin cleansing bar compositions which exhibit superior skin feel and rinsing, while maintaining acceptable skin mildness, moisturization, lather, and bar firmness properties.

SUMMARY OF THE INVENTION

This invention is an ultra mild, firm skin cleansing toilet bar comprising: 3.5% to 4.5% water, mild synthetic surfactants, moisturizers, soap, and preferably a polymeric skin feel and skin mildness aids. An ultra mild skin cleansing bar is provided which is clinically milder on the skin than water and has superior firmness, skin feel and rinsing properties. A preferred cleansing product is a toilet bar having the 3.5% to 4.5% water, and 20–70% mild surfactant, 10–40% moisturizer, 5.5–25% soap, and preferably 0.1–10% of a mixture of selected polymeric skin feel and mildness aids for mildness and rinsability. The mixture of selected polymers comprises an effective amount of a first polymeric skin feel and mildness aid which is selected primarily for its mildness and skin feel benefit and an effective amount of a second polymeric skin feel and mildness aid which is selected primarily for its skin feel and ease of rinsing benefit.

DETAILED DESCRIPTION OF THE INVENTION

The invention relates to an ultra mild skin cleansing toilet bar composition with superior firmness, moisturization, improved skin feel and rinsing benefits and excellent lather performance. This mild cleansing composition is also believed to provide superior moisturization, less skin irritation and facial tautness than commercially available toilet soap bars, synthetic toilet bars or other known surfactant based specialty skin cleansing products containing only one polymeric skin feel aid. The percentages herein are on a total composition weight basis unless otherwise specified.

A preferred composition contains: 3.5%–4.5% water, 10–40% moisturizer, e.g., free fatty acids; 40–70% of mild surfactants, e.g., alkyl glyceryl ether sulfonate (AGS) plus a co-surfactant selected from anionic alkyoyl (acyl) sarcosinates; and 0.1–4% of a mixture of polymeric skin feel and skin mildness aids selected from cationic polymers including guar gums, cellulosic resins; homopolymers and copolymers of dimethyldiallylammonium chloride and nonionic guar gums. The mixture of selected polymers comprises an effective amount of a first polymeric skin feel and mildness aid which is selected primarily for its mildness and skin feel benefit and an effective amount of a second polymeric skin feel and mildness aid which is selected primarily for its skin feel and ease of rinsing benefit. Soap is preferably used at a level of 5.5–20%.

The Surfactant

A mild surfactant as defined herein includes those which have a Relative Skin Barrier Penetration Value as defined hereinbelow of as close to zero as possible up to about 75. The mild synthetic surfactant is present in the composition at a level of 20–70%, preferably 40–70% and more preferably 50–65%. Also the synthetic surfactant and soap have ratios of 2:1 to 12:1, preferably 4:1 to 10:1 and more preferably 6:1 to 9:1.

Preferred mild anionic and amphoteric surfactants used in this invention include suitable alkyl glyceryl ether sulfonate (AGS), anionic acyl sarcosinates, methyl acyl taurates, N-acyl glutamates, alkyl glucosides, acyl isethionates, alkyl sulfosuccinate, alkyl phosphate esters, ethoxylated alkyl phosphate esters, trideceth sulfates, methyl glucose esters, protein condensates, mixtures of ethoxylated alkyl sulfates and alkyl amine oxides, betaines, sultaines, and mixtures thereof. Included in the surfactants are the alkyl ether sulfates with 1 to 12 ethoxy groups, especially ammonium and sodium lauryl ether sulfates. Alkyl chains for these surfactants are $C_8$–$C_{22}$, preferably $C_{10}$–$C_{18}$.

A preferred primary mild surfactant is sodium coco glyceryl ether sulfonate which is mild and relatively nonirritating to the skin. This has been demonstrated in in vitro nonclinical mildness testing. While desirable to incorporate into a skin cleanser for its mildness properties, this coco AGS alone does not provide optimum lather creaminess. A sodium 90/10 coconut/tallow alkyl AGS distribution is preferred for creaminess. Salts other than the sodium salt such as TEA-, ammonium- and K-AGS and chain length distributions other than 90/10 coconut/tallow are usable at moderate levels. Also, some soap is added to improve lather volume and speed of lathering. Certain secondary co-surfactants used in combination with AGS can also provide a creamier and more stable lather. These secondary surfactants must also be intrinsically mild. One secondary surfactant that has been found to be especially desirable is sodium lauroyl sarcosinate (trade name Hamposyl L, made by Hampshire Chemical).

The amphoteric betaines and sultaines can be used as the sole surfactant, but are more preferred as a co-surfactant. Nonionics cannot be used as the sole surfactant in this product because of their low foaming ability; however, they can be incorporated as a co-surfactant.

In Vitro Skin Barrier Penetration Test

The skin barrier penetration test is used to screen mild surfactants from nonmild surfactants. In this test the milder the surfactant, the lesser the skin barrier is destroyed. Skin barrier destruction is measured by the relative amount of radio-labeled water ($^3$H-H$_2$O) which passes from the test solution through the skin epidermis into the distilled water contained in the diffusate chamber. (This test is also described by T. J. Franz in the *J. Invest. Derm.*, 64, pp. 190–195, 1975, and is disclosed in detail in commonly assigned U.S. Pat. No. 4,673,525; Small/Garrison/Winkler/Seaman/Papa, issued June 15, 1987, incorporated herein by reference.)

Skin Barrier Penetration Test Values for AGS and cocoyl isethionate are given in Table 1. Water and sodium dodecylsulfate ("SDS") are the mild and harsh controls, respectively. The test results are expressed in terms of the total amount of water penetrating through the skin in 24 hours. These amounts have also been converted to a relative scale (see Table 1) with water set to zero, SDS to 100, and AGS and isethionate interpolated in between.

TABLE 1

| Treatment | Skin Barrier Penetration | |
|---|---|---|
| | Total mg Water Penetrating the Skin in 24 Hours | Relative Skin Barrier Penetration Value |
| Water Control | 12.0 ± 3.6 | 0 |
| 1% AGS[a] | 22.8 ± 7.9 | 9 |
| 1% Cocoyl Isethionate | 60.3 ± 17.7 | 40 |
| 1% SDS[b] - Reference | 131.7 ± 68.0 | 100 |

[a]AGS is sodium coco AGS
[b]SDS is sodium dodecylsulfate

A mild surfactant as defined herein includes those which have a Relative Skin Barrier Penetration Value of as close to zero as possible. Most mild surfactants have Values of from about 7 to about 75, preferably 50 or less, and more preferably 40 or less. Surfactants which have Relative Skin Barrier Penetration Values of greater than 75 can be used along with the mild surfactant at low levels in the compositions of this invention, so long as their use does not significantly change the clinical skin mildness of the total skin cleansing composition.

Moisturizers/Emollients

Moisturizers are included to provide the skin conditioning benefits and to improve the mildness of the product. The selection of the levels and types of moisturizers to be incorporated into the product is made without adversely affecting the stability of the product or its in-use characteristics, thereby delivering good moisturization and lather.

The term "moisturizer" is often used within the cosmetic industry without very exact definition. The term is sometimes used as synonymous with emollient, and is then meant to describe a material which imparts a smooth and soft feeling to the skin surface.

There are two ways of reducing water loss from the stratum corneum. One is to deposit on the surface of the skin an occlusive layer which reduces the rate of evaporation. The second method is to add nonocclusive hygroscopic substances to the stratum corneum which will retain water, and make this water available to the stratum corneum to alter its physical properties and produce a cosmetically desirable effect. Nonocclusive moisturizers also function by improving the lubricity of the skin.

Both occlusive and nonocclusive moisturizers can work in the present invention. Some examples of moisturizers are long chain fatty acids, liquid water-soluble polyols, glycerin, propylene glycol, sorbitol, polyethylene glycol, ethoxylated/propoxylated ethers of methyl glucose (e.g., methyl gluceth-20) and ethoxylated/-propoxylated ethers of lanolin alcohol (e.g., Solulan-75).

The moisturizers useful in the present invention are used at a level of 10% to 40% by weight of the composition. The preferred and more preferred levels of moisturizers are, respectively, 10% to 30% and 12% to 25%. The preferred moisturizers are the coco and tallow fatty acids. Some other preferred moisturizers are the nonocclusive liquid water-soluble polyols and the essential amino acid compounds found naturally in the skin. The most preferred moisturizer is a mixture of stearic and lauric acids having a ratio of from 2:1 to 1:1. These moisturizers also aid in solid bar integrity at said levels.

The moisturizer, at these levels, provides superior moisturization. In the composition of this invention the high level of moisturizer with soap can also provide an enhanced lather and mildness.

The moisturizer to soap ratios are preferably 1:1 to 7:1 and, more preferably, 1:1 to 4:1.

Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other non-occlusive moisturizers include hexadecyl, myristyl, isodecyl or isopropyl esters of adipic, lactic, oleic, stearic, isostearic, myristic or linoleic acids, as well as many of their corresponding alcohol esters (sodium isostearoyl-2-lactylate, sodium capryl lactylate), hydrolyzed protein and other collagen-derived proteins, aloe vera gel and acetamide MEA.

Some occlusive moisturizers include petrolatum, mineral oil, beeswax, silicones, lanolin and oil-soluble lanolin derivatives, saturated and unsaturated fatty alcohols such as behenyl alcohol, squalene and squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Other examples of both types of moisturizrrs are disclosed in "Emollients—A Critical Evaluation," by J. Mausner, Cosmetics & Toiletries, May 1981, incorporated herein by reference.

Polymeric Skin Feel and Skin Mildness Aids

While the firmness benefit realized with a low moisture content of 3.5% to 4.5% water can be realized in bars without a polymeric skin feel aid, the presence of at least one polymeric skin feel aid is highly desirable.

In the preferred embodiment a selected mixture of at least two polymeric skin feel and mildness aids are used in the present invention. They can be selected from cationic, anionic, amphoteric, and the nonionic polymers suitable for contact with human skin. The mixture comprises an effective amount of a first polymeric skin feel and mildness aid which is selected primarily for its mildness and skin feel benefit and an effective amount of a second polymeric skin feel and mildness aid which is selected primarily for its skin feel and ease of rinsing benefit.

The terms "first" and "second" polymeric skin feel aid as used here connote one polymer or a mixture of polymers selected for the desired mildness or ease of rinsing benefit respectively. The first and second polymeric aids are selected to enhance synergistically their respective mildness and ease of rinsing benefits for an overall improved bar.

Polymer Skin Feel and Ease of Rinsing Screening Test

Purpose

To screen polymers for skin feel during use and ease of rinsing.

Test Method

Polymers are tested in toilet bar formulations using a Blind, Round Robin, Pair Test (all test variables are tested vs. a comparable bar with 3% JR-400 which is desirable for mildness, but less desirable because of its slipperiness during use and when rinsing). Three expert judges are recommended. Prior to evaluating the bars, all products are re-coded by an independent technician to make sure the judges testing the products are blind (i.e., they do not know which samples are being evaluated). Each judge evaluates six different products in fourteen different product pairs, including several marked pairs and in reverse order using different codes to measure reproducibility. Each judge uses the following washing procedure to evaluate each bar, indicating level of difference between each product pair for skin feel both during use and during rinsing on a zero to eight grading scale; zero being "No difference" and eight being "Very large difference." A larger difference indicates less slipperiness and easier rinsing.

Polymer JR-400 and Jaguar C-14S at 3% level each give a very large slipperiness feel during rinsing. Substitution of Merquat 550 or Mirapol A-15 for JR-400 reduces the polymer feel in terms of reduced slipperiness and improves the rinsing properties.

Washing Procedure (Using City Water [7-9 grain hardness] between 95° F.-100° F.)
1) Wash hands with IVORY ® bar soap prior to using each bar.
2) Wet bar and hands.
3) Rotate bar in hands for three complete revolutions (6 one-half bar revolutions).
4) Add a little water to hands.
5) Rotate one hand in a circular motion over the other hand five times.
6) Work lather for a minute.
7) Rinse hands for thirty seconds.
8) Repeat steps one through seven for the second product.
9) After using both bars fill out the questionnaire provided.
10) Wait two hours before evaluating next pair of test bars.

Bars
Bar without polymer
Bar with 1.5% JR-400
Bar with 3.0% JR-400
Bar with 3.0% Jaguar C-14S
Bar with 3.0% Mirapol A-15
Bar with 3.0% Merquat 550

1. During use the order of relative differences in feel (less slipperiness) as compared to 3% JR-400 is as follows: No polymer, 3.0% Mirapol, 1.5% JR-400, 3.0% Merquat, 3% Jaguar, and 3% JR-400.

All polymer formulations, except 3.0% Jaguar are significantly (p=0.05) different from, or less slippery than, 3% JR-400.

2. During rinsing, the order of relative differences in feel (less slipperiness) as compared to 3% JR-400 is as follows: 3% Mirapol, No polymer, 1.5% JR-400, 3.0% Merquat, 3% Jaguar, and 3% JR-400.

All polymer formulations, except 3.0% Jaguar are significantly (p=0.05) different from 3% JR-400.

The molecular weight ranges for the polymeric skin feel and mildness aids are: 1,000 to 4,000,000, preferably 2,000 to 3,800,000, and more preferably 2,500 to 3,000,000.

The amount of the selected mixture of polymeric skin feel and mildness aids found useful in the composition of the present invention is from about 0.01% to about 10%, preferably from about 0.3% to about 4%. The selected first and second polymers present in the preferred bars of this invention preferably have a ratio of about 10:1 to 1:10, more preferably 4:1 to 1:4, and 3:1 to 1:3.

Some examples of high molecular weight polymeric skin feel and skin mildness aids are: nonionic guar gums; Merquats 100 and 550, made by Merck & Co., Inc; Jaguar C-14-S made by Stein Hall; Mirapol A15 made by Miranol Chemical Company, Inc.; and Galactasol 811, made by Henkel, Inc.; plus others, are usable. Some polymers also provide enhanced creamy lather benefits.

The nonionic polymers found to be useful include the nonionic polysaccharides, e.g., nonionic hydroxypropyl guar gums, offered by Celanese Water Soluble Polymers, a Division of Celanese Corp. A preferred nonionic hydroxypropyl guar gum material is JAGUAR ® HP-60 having molar substitution of about 0.6. Another class of useful nonionics is the cellulosic nonionic polymers, e.g., HEC and CMC.

Some preferred polymeric aids selected as mildness aids are:
1. JR400 and any higher or lower molecular weight versions. Name: quaternary ammonium salt of hydroxyethylcellulose.
2. Jaguar C15, C14S, C13, C17 and any higher or lower molecular weight versions.
   Name: Guar hydroxypropyltrimonium chloride.
3. Jaguar HP60 and any higher or lower molecular weight versions.
   Name: Hydroxypropyl guar
4. Celquat H60,L200 and any higher or lower molecular weights.
   Name: Diallyldimonium chloride/hydroxyethylcellulose copolymer.

Some preferred low slipperiness polymeric skin feel aids are:
1. Merquat 550 and any higher or lower molecular weight versions.
   Name: Polymeric quaternary ammonium salt of acylamide and dimethylediallyl ammonium chloride monomers.
2. Merquat 100 and any higher or lower molecular weight versions.
   Name: Poly (dimethyldiallyl ammonium chloride).
3. Merquat S and any higher or lower molecular weight versions.
   Name: polymeric quaternary ammonium salt of acylamide and dimethyldiallyl ammonium chloride and diethyldiallyl ammonium chloride monomers.
4. Mirapol A-15
   Name: Poly[N-[3-(dimethylammonio)propyl]-N'-[3-ethyleneoxyethylenedimethylammonio)propyl]urea dichloride]:

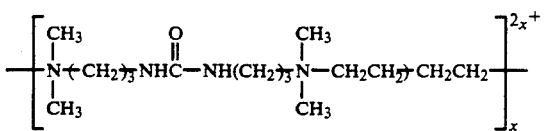

wherein x is about 6.

The mixture of polymers employed in this invention are selected to provide a desirable silky, soft, smooth in-use feeling with a minimal slippery feel during and after rinsing. While not being bound to any theory, it is believed that certain cationic polymers chemically interact with the anionic surfactants (e.g., AGS and sarcosinates) to form complexes which may enhance the mildness to skin characteristics of the already mild surfactants. Also, there is reason to believe that the positively charged cationic polymers can bind with negatively charged sites on the skin to provide a soft skin feel after use. Not to be bound by any theory, it is believed that the greater the charge density of the cationic polymer, the more effective it is for skin feel benefits Other suitable cationic polymers are copolymers of dimethylaminoethylmethacrylate and acrylamide and copolymers of dimethyldiallylammonium chloride and acrylamide in which the ratio of the cationic to neutral monomer units has been selected to give a copolymer having a cationic charge. Yet other suitable types of cationic polymers are the cationic starches, e.g., Sta-Lok ® 300 and 400 made by Staley, Inc.

A more complete list of cationic polymers useful in the present invention is described in U.S. Pat. No. 4,438,095, to Grollier/Allec, issued Mar. 20, 1984, incorporated herein by reference. Some of the more preferred cationics are listed in Col. 3, section 2; Col. 5, section 8; Col. 8, section 10; and Col. 9, lines 10-15 of the Grollier/Allec patent, incorporated herein by reference.

Soaps

The benefit of using the mixed polymer disclosed herein can be realized in bar compositions without soap, but some soap is highly perferred.

Soaps are included in the compositions of this invention for improved lather, particularly under heavy soil loads. It is also surprising that the soap as used in the compositions of this invention provide clinical benefits for less skin dryness at levels up to 25% and less skin irritation (erythema) at levels up to 15%.

Soaps can be used at levels of 5.5-25%, preferably 6-15%, and most preferably at a level of 6-8%. The soaps are preferably made in situ via adding a base, e.g., NaOH, to convert free fatty acids in the composition mix. A minor amount of soap, about 0.1-0.5% is present as a by-product of the synthetic surfactant. See the process for making an ultra mild bar set out below.

The preferred ultra mild skin cleansing bar comprises: 20-50% mild synthetic surfactant; 3.5%-4.5% water; 10-40% moisturizer, 5.5-25% soap, and, preferably, 0.1-10% of the selected mixture of polymeric skin feel aids. The synthetic surfactant and soap has a ratio of from 2:1 to 12:1; the moisturizer to soap has a ratio of from 11 to 7:1. Preferably the synthetic to soap ratio is 4:1 to 10:1, and more preferably 6:1 to 9:1. The preferred moisturizer to soap ratio is from 2:1 to 4:1.

The soap is preferably made in situ from free fatty acids and a base selected from magnesium hydroxide and potassium hydroxide, preferably sodium hydroxide and triethanolamine. The preferred soap level is 6-15% of the composition, particularly in ultra mild skin cleansing compositions which contain from 10-30% fatty acids. Particularly preferred fatty acids are mixtures of stearic and lauric acids having a ratio of from 2:1 to 1:1.

Optionals

The usual optionals can be used in the composition of the present invention.

Perfumes may be used in formulating the skin cleansing products, generally at a level of about 0.1% to about 1.5% of the composition. Colorants, and also fillers such as talc and clay, may also be used. Preservatives, e.g., EDTA, generally at a level of less than 1% of the composition, may be incorporated in the cleansing products to prevent microbiological growth. Anti-bacterials can also be incorporated, usually at levels up to 1.5%.

Process for Making the Ultra Mild Low Moisture Toilet Bar

In order to make the product, an analysis of the surfactant paste is needed. To illustrate the process, an AGS paste with the following nominal analysis will be used.

Cationic Titration for $SO_3$ = 48.5% AGS
NaCl = 1.5%
Moisture = 43%

After the composition of the AGS paste is determined, the crutcher mix is calculated using the AGS/sarcosinate ratio of 4:1, 55% moisture in the crutcher mix and about 4.0% NaCl in the final bar.

Crutching

Assuming 200 lb (90.8 Kg) crutcher mix and the above AGS analysis.

1. Heat crutcher tank by adding 200.F (93.C) hot water and adjusting steam and water valves.
2. Add 89.16 lbs. (40.48 Kg) of AGS paste.
3. Turn on agitator and recirculation pump.
4. When the AGS temperature is 130.F (54 C) add 13.22 lbs. (6.00 Kg) of stearic acid.
5. When the crutcher mix temperature is back up to 130° F. (54° C.) add 2.15 lbs. (976g) of 50% NaOH.
6. Add 2-3 gal. (7.6-11.4 liters) of hot water (160°-180° F., 71°-82° C.) as needed to thin the crutcher mix to obtain good mixing.
7. Allow the crutcher contents to mix for about 20 minutes and maintain the temperature at 130°-140° F. (54°-60° C.).
8. Add 11.42 lbs. (5.18 Kg) of Hamposyl L-95 $C_{12}$ sarcosinate.
9. Add 2-3 gal. (7.6-11.4 liters) of hot water as needed for good mixing.
10. Maintain 140° F. (60° C.).
11. Add 0.48 lbs. (218 grams) JR-400 powder to the crutcher.
12. Add 11.90 lbs. (5.40 Kg) of an 8.0% Merquat solution to the crutcher.
13. Add 0.22 lbs. (101 g) of $TiO_2$.
14. Add 1.16 (527 g) of NaCl.
15. Add 8.0 lbs. (3.63 Kg) of lauric acid.
16. Add more hot water to get to 55% H20 in the crutcher.
17. Mix for at least 20 min. and bring the crutcher mix temperature up to 140° C. (60° C.).

Drying

The crutcher mix is dried and cooled using a combination flash chamber and chill roll. The crutcher mix is first heated to approximately 300° F. (149° C.) by a heat exchanger and then flashed dried in a chamber at the top of the chill roll. From the flash chamber the hot, dried mix drops onto the nip of the chill roll and applicator roll. The chill roll/applicator roll nip is set to give a uniformly thin, cool (85°-95° F., 29.4°-35° C.) flake on the chill roll. Typical moisture for the flake is 2-3%. The ways to regulate the moisture, in order of preference, are (1) increasing or decreasing steam pressure on the heat exchanger, (2) increasing or decreasing crutcher mix rate to the heat exchanger, or (3) increasing or decreasing crutcher mix temperature to the heat exchanger.

Amalgamating

The flakes are weighed and mixed in a batch amalgamator to obtain a uniform flake sample for moisture analysis. Once the percent water is known, water and perfume are added to bring the flakes up to final target moisture level of 3.5–4.5% water. About ½% extra water is added to allow for losses during processing. The sticky, perfumed flakes are transferred to the mill hopper.

Milling

The 3-roll soap mills are set up with the first roll at 100° F. (38° C.) and the other 2 rolls at about 70° F. (21° C.). The soap is passed through the mills several times and forms sticky flakes. These flakes are put into a sealed plastic bag and placed in the 100° F. (38° C.) constant temperature room overnight. The flakes are milled one final time prior to plodding.

Plodding and Stamping

The plodder is set up with the barrel temperature at ambient to cold and the nose temperature at 120°–130° F. (49°–54° C.). The ideal plodder is a dual stage plodder that allows use of a vacuum of about 15–25 in. Hg. The plugs should be cut in 5" sections and stamped with a cold die block and stamp using a die liquor such as alcohol.

Clinical Assessment of Ultra Mild Toilet Bar

A clinical test procedure used to evaluate toilet bar formulations for skin mildness is set out in commonly assigned U.S. Pat. No. 4,673,525, supra, incorporated by reference in its entirety.

EXAMPLES

The following examples of low moisture toilet bars are made using the above procedure. The level of water in the final bar must be between 3.5% and 4.5% to provide the improved bar firmness. If the level of water is too low, lather suffers; if too high, firmness suffers. Low moisture bars without the polymers, or with one polymer, are preferred over high moisture bars of the same types for the same reasons.

TABLE 2

| 4 oz. (or 113 gm.) Bar Formulation Targets | | | |
|---|---|---|---|
| Examples | G | H | J |
| Ingredients | | | |
| NaAGS | 46.39 | 46.39 | 46.39 |
| NaC12 Sarcosinate | 11.08 | 11.08 | 11.08 |
| Stearic Acid | 10.77 | 10.77 | 10.77 |
| Lauric Acid | 7.18 | 7.18 | 7.18 |
| JR-400 | — | 0.50 | 1.50 |
| Merquat 550 | 0.50 | 1.00 | — |
| Jaguar C-15 | 1.00 | — | — |
| Dextrin | — | — | — |
| Unsulfonated Alcohol | 4.67 | 4.67 | 4.67 |
| Na Laurate | 0.50 | 0.50 | 0.50 |
| Na Soap (60/40 T/C) | 7.48 | 7.48 | 7.48 |
| NaCl | 3.99 | 3.99 | 3.99 |
| Na2SO4 | 1.5 | 1.5 | 1.5 |
| TiO2 | 0.20 | 0.20 | 0.20 |
| Perfume | 0.75 | 0.75 | 0.75 |
| Water | 3.99 | 3.99 | 3.99 |
| Total | 100.00 | 100.00 | 100.00 |

TABLE 3

| | Analytical Data | | |
|---|---|---|---|
| | G Actual | H Actual | J Actual |
| % H2O | 4.39 | 3.98 | 4.02 |
| % SO3 | 9.65 | 9.76 | ?.67 |
| % AGS | 45.59 | 46.15 | 45.70 |
| % FFA (as CnFA)* | 13.5 | 13.1 | 14.4 |
| % NaCl | 3.84 | 3.98 | 3.84 |

*Free fatty acid

Laboratory Assessment of Bar Performance

The following test procedures are used to evaluate the critical bar performance attributes of lather volume and bar firmness during use.

Bar Soap Firmness Test

The bar soap firmness test measures three quantitative parameters of bar firmness after sitting in a wet soap dish for 16 hours: (1) depth of bar surface softening; (2) amount of bar messiness by weight percent of initial bar weight; and (3) smear value.

Equipment

The following equipment is used:
1. "Alathon" rectangular plastic soap dishes (U.S. Pat. No. 2,842,178) with low ridges.
2. Precision Scientific Co. penetrometer with ball shaft, 300 gram weight.
3. Analytical weight balance.
4. Scraper or spatula for removing gelatinous layer.
5. Paper towels.

Procedure

The following procedure is used:
1. Test bar(s) are weighed to establish an initial dry weight data point.
2. If desired, initial dry bar hardness/softness may be determined by penetrometer with cone shaft and 200 gram weight for penetration measurement. A penetrometer value of 2.7 or less is preferred.
3. Bar(s) are placed centrally on soap dishes containing 5 ml. of distilled water at room temperature. Rock the dish to break water tension.
4. Store overnight (approximately 18 hours) in standard room conditions of temperature and humidity (80° F./80% RH).
5. Next morning, remove bar(s) with a careful vertical lift and invert for testing.
6. Run ball penetrometer reading on the gelatinous surface, generally three readings in a triangular design; record the average mm depth reading of gelatinous layer. The shaft ball is cleaned with a tissue after each reading.
7. Bar(s) are then carefully scraped to remove the gelatinous layer down to the solid surface. Do not use enough force to remove any of the solid surface area. Slight remaining gelatinous soap may be wiped from bar with paper towels until surface appears firm and somewhat dry.
8. Bar(s) are then allowed to openly dry out on bench surface for no more than one hour.
9. Bar(s) are then weighed to determine the difference from the initial dry untested weight. The weight difference divided by the original weight is calculated into % weight loss or % gelatinous smear weight. Data is recorded.
10. Comparison of any given series of data points obtained will illustrate a formula characteristic that may tend to relate to poorer smear or "messiness" attribute. Averaging of historical data on control type formulas (such as an existing National brand formula) can be used to establish a benchmark for comparison.

Bar Soap Handwash Lather Volume Test

The handwash lather test is used to provide in-use lather volume measurements for the lather performance of skin cleansing bars. The test measures both the ultimate lather volume generated and the volume which is generated after a very short lathering period (to reflect lathering ease). The lather volumes are generated under both soil-loaded and nonloaded conditions.

Synthetic soil is used for the soil-loaded lather volume test reported herein. Its formula and procedure for making it are set out below.

TABLE 4

| Synthetic Soil | |
|---|---|
| Ingredients | Wt. % |
| Hyfac 430[a] | 1.87 |
| Lauric Acid[b] | 1.42 |
| Neo-fat 14[c] | 5.68 |
| Neo-fat 16[d] | 11.16 |
| Neo-fat 18[e] | 5.40 |
| Neo-fat 90-04[f] | 9.81 |
| Industrene 226[g] | 1.26 |
| Paraffin Wax | 7.30 |
| Squalane[h] | 3.70 |
| Lanolin Anhydrous | 19.40 |
| Coconut Oil | 3.30 |
| Tallow | 29.70 |
| | 100.00% |

[a]Emery Industries, Inc., Cincinnati, Ohio
[b]Emery Industries, Inc., Cincinnati, Ohio
[c]Armour Industrial Chemical Co., Chicago, Illinois
[d]Armour Industrial Chemical Co., Chicago, Illinois
[e]Armour Industrial Chemical Co., Chicago, Illinois
[f]Armour Industrial Chemical Co., Chicago, Illinois
[g]Humko Products, Memphis, Tennessee
[h]Robeco Chemicals, Inc., New York, New York Procedure
1. Heat above materials together stirring continuously between 160°-175° F.
2. Mix 25 parts of above formula with 25 parts of a 5% to 80% tallow/20% coconut soap solution and 50 parts of distilled water at 150° F.
3. Cool mixture to room temperature while stirring constantly.
4. Store in covered glass container.

Equipment
The following equipment is used:
1. Water source and sink with temperature control. The water source should be medium hardness (6-9 grain/gallon) for most testing, although water of lower and higher hardness can be used for special purposes.
2. Synthetic soil (see Table 4).
3. Paper towels.
4. Test bars.
5. Control bars (i.e., usually marketed brands such as CAMAY ® or the bar of Example D in U.S. Pat. No. 4,673,525, Small et al., incorporated herein by reference).

Procedure
The following procedure is used:
1. Set temperature at 95°-100° F.
2. Rub 0.22 cc of soil on hands (if doing soil-loaded test).
3. Wet hands.
4. Rotate bar 3 times in both hands.
5. Add a little water, rub both hands 5 times.
6. Rotate hands 3 times (without soap), grade for flash volume.
7. Rotate 7 more times, grade for ultimate volume.
8. Collect lather and deposite on sink top.
9. Compare volume with standard bar target volume and assign grade.

| Grading Scale | |
|---|---|
| Non-Soil Loaded | Soil-Loaded |
| 10 - Very much higher than target | |
| 9 - Higher than target | |
| 8 - Target volume* | Very much higher than target |
| 7 - Lower than target | Higher than target |
| 6 - Very much lower than target | Target volume* |
| 5 - Unacceptably lower than target | Slightly lower than target |
| 4 - Unacceptably lower than target | Lower than target |
| 3 - Unacceptably lower than target | Very much lower |
| 2 - Unacceptably lower than target | Unacceptably low |

*Based on 50 tallow/50 coconut - 7% free fatty acid bar.

TABLE 5

| | Bar Formulations | | | |
|---|---|---|---|---|
| Example | JR-400 Wt. % | Merquat 550 Wt. % | Mirapol A-15 Wt. % | Jaguar C-14 Wt. % |
| 1 | 1.5% | — | — | — |
| 2 | 0.5% | 1.0% | — | — |
| 3 | 1.0% | 0.5% | — | — |
| 4 | 1.0% | — | 0.5% | — |
| 5 | — | 0.5% | — | 1.0% |

TABLE 6

| | Hand Lather | | | |
|---|---|---|---|---|
| | Ultimate Volume | | Flash Volume | |
| Example | w/o Soil | Soil | w/o Soil | Soil |
| 1 | 8 | 5.0 | 8 | 4.0 |
| 2 | 8.5 | 4.0 | 8.5 | 3.5 |
| 3 | 8 | 3.0 | 7.5 | 2.5 |
| 4 | 8 | 4.0 | 8 | 3.5 |
| 5 | 8.5 | 4.5 | 8.5 | 4.0 |

The results in Tables 5 and 6 show the importance of achieving a proper balance of polymers for lather performance. The lather also suffers when the moisture level is below 3.5%.

Thus, an improved, ultra mild, firm, skin cleansing bar can be made with a low moisture content, selected mild synthetic surfactants; selected moisturizers; selected levels of soap; and a selected mixture of polymeric skin feel and mildness aids.

What is claimed is:

1. An ultra mild firm, stamped, toilet synbar comprising:
A. 20-70% mild synthetic surfactant; said mild synthetic surfactant having a Relative Skin Barrier Penetration Value of less than about 40;
B. 10-40% moisturizer;
C. 5.5-25% soap;
D. 0.1-5% of a polymeric skin feel and mildness aid;
E. 3.5%-4.5% water; and
wherein said synbar has improved bar firmness over comparable bars having higher water levels; and wherein said polymeric skin feel and mildness aid are selected from the group consisting of: quaternary ammonium salt of hydroxyethylcellulose;

guar hydroxypropyltrimonium chloride; hydroxypropyl guar, and diallyldimonium chloride/hydroxyethylcellulose copolymer; polymeric quaternary ammonium salt of acylamide and dimethyldiallyl ammonium chloride monomers; poly (dimethyldiallyl ammonium chloride); and polymers having the following structural formula:

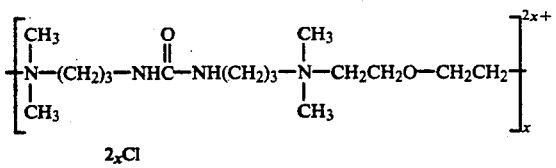

$2_xCl$ wherein x is about 6; and mixtures thereof
wherein said synthetic surfactant and said soap have a ratio of from 2:1 to 12:1, and
wherein said moisturizer to soap has a ratio of from 1:1 to 7:1.

2. The ultra mild, firm toilet bar of claim 1 wherein said polymeric skin feel aid is cationic.

3. The ultra mild, firm toilet bar of claim 1 wherein said bar contains at least one polymeric aid selected from the group consisting of cationic and nonionic polysaccharides; cationic and nonionic homopolymers and copolymers derived from acrylic and/or methacrylic acid; cationic copolymers of dimethyldiallylammonium chloride and acrylic acid; cationic homopolymers of dimethyldiallylammonium chloride; cationic polyalkylene and ethoxypolyalkylene imines.

4. The ultra mild, firm toilet bar of claim 1 wherein said bar contains a mixture of polymeric skin feel and mildness aids selected from the group consists of: quaternary ammonium salt of hydroxyethylcellulose and polymeric quaternary ammonium salt of acylamide and dimethyldiallyl ammonium chloride monomers and mixtures thereof.

5. The ultra mild, firm toilet bar of claim 1 wherein said mild surfactant is selected from the group consisting of:
alkyl glyceryl ether sulfonate;
anionic acyl sarcosinates;
methyl acyl taurates;
N-acyl glutamates;
alkyl glucosides;
acyl isethionates;
alkyl sulfosuccinate;
alkyl phosphate ester;
alkyl ether sulfate;
ethoxylated alkyl phosphate esters;
methyl glucose esters;
protein condensates;
mixtures of ethoxylated alkyl sulfates and alkyl amine oxides;
betaines;
sultaines; and
mixtures thereof.

6. The ultra mild, firm toilet bar of claim 1 wherein said mild surfactant is an alkyl glyceryl ether sulfonate /sarcosinate mix having ratio of 1:1 to 5:1.

7. The ultra mild toilet bar of claim 5 wherein soap is 6-15% of said toilet bar; and wherein said bar contains from 40-70% of mild surfactants, from 10-30% of said moisturizer, said moisturizer being fatty acids; and wherein said mild surfactants are made with a base selected from NaOH and triethanolamine.

8. The ultra mild toilet bar of claim 7 wherein said fatty acids are stearic and lauric having a ratio of from 4:1 to 1:1.

9. An ultra mild, stamped, toilet bar comprising:
A. 20-70% mild synthetic surfactant; said mild synthetic surfactant having a Relative Skin Barrier Penetration Value of less than about 40;
B. 10-40% moisturizer;
C. 5.5-25% soap; and
D. 0.1-5% of a mixture of at least two polymeric skin feel and mildness aids wherein an effective amount of a first of said aids is selected primarily for skin mildness and an effective amount of a second of said aids is selected primarily for its low slipperiness in rinsing; wherein said ratio is 4:1 to 1:4; and wherein said first polymeric skin feel and mildness aid are selected from the group consisting of: quaternary ammonium salt of hydroxyethylcellulose; guar hydroxypropyltrimonium chloride; hydroxypropyl guar, and diallyldimonium chloride/hydroxyethyl-cellulose copolymer and mixtures thereof; and said second polymeric skin feel and mildness aid is selected from the group consisting of poly (dimethyldiallyl ammonium chloride); polymeric quaternary ammonium salt of acylamide and dimethyldiallyl ammonium chloride monomers; and polymers having the following structural formula:

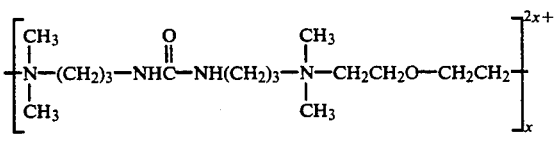

$2_xCl$ wherein x is about 6; and mixtures thereof
wherein said synthetic surfactant and said soap have a ratio of from 2:1 to 12:1, and
wherein said moisturizer to soap has a ratio of from 1:1 to 7:1.

10. The ultra mild toilet bar of claim 9 wherein said first and second polymeric skin feel aids have a ratio of 10:1 to 1:10.

11. The ultra mild toilet bar of claim 10 wherein said ratio of said polymer is from 1:3 to 3:1.

12. The ultra mild toilet bar of claim 9 wherein at least one of said polymeric skin feel aids is cationic.

13. The ultra mild toilet bar of claim 9 wherein said mixture has at least two cationic polymeric skin feel and mildness aids.

14. The ultra mild toilet bar of claim 9 wherein at least one of said polymeric aids is selected from the group consisting of cationic and nonionic polysaccharides; cationic and nonionic homopolymers and copolymers derived from acrylic and/or methacrylic acid; cationic copolymers of dimethyldiallylammonium chloride and acrylic acid; cationic homopolymers of dimethyldiallylammonium chloride; cationic polyalkylene and ethoxypolyalkylene imines.

15. The ultra mild toilet bar of claim 9 wherein said mixture of polymers is present at 0.3-4% by weight and has a ratio of 3:1 to 1:3

16. The ultra mild toilet bar of claim 9 wherein said mixture of polymeric skin feel and mildness aids are: quaternary ammonium salt of hydroxyethylcellulose and polymeric quaternary ammonium salt of acylamide and dimethyldiallyl ammonium chloride monomers.

17. The ultra mild toilet bar of claim 9 wherein said mild surfactant is selected from the group consisting of:
alkyl glyceryl ether sulfonate;
anionic acyl sarcosinates;
methyl acyl taurates;
N-acyl glutamates;
alkyl glucosides;
acyl isethionates;
alkyl sulfosuccinate;
alkyl phosphate ester;
alkyl ether sulfate;
ethoxylated alkyl phosphate esters;
methyl glucose esters;
protein condensates;
mixtures of ethoxylated alkyl sulfates and alkyl amine oxides;
betaines;
sultaines; and
mixtures thereof.

18. The ultra mild toilet bar of claim 17 wherein said mild surfactant is an alkyl glyceryl ether sulfonate /sarcosinate mix having ratio of 1:1 to 5:1.

19. The ultra mild toilet bar of claim 18 wherein said alkyl glyceryl ether sulfonate/sarcosinate has a ratio of 2:1 to 4:1.

20. The ultra mild toilet bar of claim 9 wherein said bar also contains a co-surfactant selected from the group consisting of nonionic, amphoteric betaine or amphoteric sultaine, and wherein the mild surfactant and the co-surfactant have a ratio of 1:1 to 5:1, and said mild surfactant is other than betaine or sultaine.

21. The ultra mild toilet bar of claim 9 wherein said toilet bar contains from 5.5-20% soap and wherein said soap is made in situ from free fatty acids and a base selected from KOH, $Mg(OH)_2$, NaOH and triethanolamine.

22. The ultra mild toilet bar of claim 21 wherein soap is 6-15% of said toilet bar; and wherein said bar contains from 10-30% fatty acids; and wherein said base is selected from NaOH and triethanolamine.

23. The ultra mild toilet bar of claim 22 wherein said fatty acids are stearic and lauric having a ratio of from 4:1 to 1:1.

24. The ultra mild toilet bar of claim 23 wherein said moisturizer is a mixture of stearic and lauric acids having a ratio of from 2:1 to 1:1 and is present in said bar at a level of from 15-20%.

25. The ultra mild toilet bar of claim 9 wherein said moisturizer is present at a level of 10-30% of said composition.

26. An ultra mild, stamped, toilet synbar comprising:
A. 20-70% mild synthetic surfactant; said mild synthetic surfactant having a Relative Skin Barrier Penetration Value of less than about 40;
B. 10-40% moisturizer;
C. 5.5-25% soap; and
D. 3.5%-4.5% water; and wherein said synbar has improved firmness over comparable synbars having higher water levels wherein said synthetic surfactant and said soap have a ratio of from 2:1 and wherein said moisturizer to soap has a ratio of from 1:1 to 7:1.

27. The ultra mild, stamped, toilet bar of claim 26 wherein said synbar contains a mixture of alkyl glyceryl ether sulfonate and sarcosinate at a ratio of 2:1 to 4:1.

* * * * *